(12) United States Patent
Lerch

(10) Patent No.: US 10,687,778 B2
(45) Date of Patent: Jun. 23, 2020

(54) POSITIONING OF AN EXAMINATION OBJECT FOR AN IMAGING METHOD

(71) Applicant: Siemens Healthcare GmbH, Erlangen (DE)

(72) Inventor: Daniel Lerch, Weilersbach (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 321 days.

(21) Appl. No.: 15/614,717

(22) Filed: Jun. 6, 2017

(65) Prior Publication Data

US 2017/0354385 A1 Dec. 14, 2017

(30) Foreign Application Priority Data

Jun. 8, 2016 (DE) .......................... 10 2016 210 131

(51) Int. Cl.
*A61B 6/03* (2006.01)
*A61B 6/04* (2006.01)
(Continued)

(52) U.S. Cl.
CPC ............... *A61B 6/54* (2013.01); *A61B 5/0077* (2013.01); *A61B 5/70* (2013.01); *A61B 6/032* (2013.01);
(Continued)

(58) Field of Classification Search
CPC ........... A61B 6/032; A61B 6/035; A61B 6/04; A61B 6/4435; A61B 6/4441; A61B 6/48;
(Continued)

(56) References Cited

U.S. PATENT DOCUMENTS 7,016,522 B2 *  3/2006  Bani-Hashemi ......... A61B 6/04
                                                          250/363.04
7,251,845 B2 *  8/2007  Schaller ............... A61B 5/0555
                                                              5/613
(Continued)

FOREIGN PATENT DOCUMENTS

DE    102004021972 A1    12/2005
DE    102012201798 A1     8/2013
(Continued)

OTHER PUBLICATIONS

German Office Action #102016210131.5 dated Mar. 2, 2017.
Chinese Office Action and English translation thereof dated Apr. 1, 2020.

*Primary Examiner* — Allen C. Ho
(74) *Attorney, Agent, or Firm* — Harness, Dickey & Pierce, P.L.C.

(57) ABSTRACT

A method is described for positioning of an examination object for an imaging method. The method is used to record an external image of externally visible features of the examination object. The recording of the external image is used as the basis for determining a position and/or orientation of at least one part of the examination object assigned to the imaged features. Subsequently, a check is performed as to whether the determined position and/or orientation of the at least one part of the examination object conforms to a reference position and/or reference orientation. Finally, if the determined position and/or orientation of the at least one part of the examination object does not conform to the reference position and/or reference orientation, the position and/or orientation of the at least one part of the examination object is corrected. Also described is an object-positioning facility. Furthermore, an imaging medical facility is described.

25 Claims, 3 Drawing Sheets

(51) Int. Cl.
  *A61B 6/00* (2006.01)
  *A61B 5/00* (2006.01)
  *G01R 33/30* (2006.01)
  *G01R 33/28* (2006.01)
  *A61B 5/055* (2006.01)

(52) U.S. Cl.
  CPC .............. *A61B 6/035* (2013.01); *A61B 6/04* (2013.01); *A61B 6/0407* (2013.01); *A61B 6/0414* (2013.01); *A61B 6/42* (2013.01); *A61B 6/4208* (2013.01); *A61B 6/4258* (2013.01); *A61B 6/44* (2013.01); *A61B 6/4429* (2013.01); *A61B 6/4435* (2013.01); *A61B 6/4441* (2013.01); *A61B 6/48* (2013.01); *A61B 6/488* (2013.01); *A61B 6/542* (2013.01); *A61B 6/544* (2013.01); *A61B 6/545* (2013.01); *A61B 6/589* (2013.01); *G01R 33/30* (2013.01); *A61B 5/0555* (2013.01); *G01R 33/283* (2013.01)

(58) Field of Classification Search
  CPC ....... A61B 6/488; A61B 6/589; A61B 6/0407; A61B 6/0414; A61B 6/42; A61B 6/4208; A61B 6/4258; A61B 6/44; A61B 6/4429; A61B 6/54; A61B 6/542; A61B 6/544; A61B 6/545
  USPC .......... 378/20, 196, 197, 162–166, 204–209
  See application file for complete search history.

(56) References Cited

U.S. PATENT DOCUMENTS

| | | | | |
|---|---|---|---|---|
| 7,343,189 B2* | 3/2008 | Kagermeier | ............ | A61B 6/08 378/20 |
| 7,640,607 B2* | 1/2010 | Guertin | ............... | A61B 6/547 5/601 |
| 7,697,147 B2* | 4/2010 | Kindlein | ................ | A61B 6/08 356/601 |
| 7,806,589 B2* | 10/2010 | Tashman | .............. | A61B 5/1038 378/193 |
| 8,042,209 B2* | 10/2011 | D'Souza | .............. | A61N 5/1049 5/610 |
| 8,130,384 B2* | 3/2012 | Kindlein | ................ | A61B 6/08 356/601 |
| 8,176,585 B1* | 5/2012 | Isham | ................. | A61G 13/121 5/621 |
| 8,199,876 B2* | 6/2012 | Graumann | .............. | A61B 6/02 378/63 |
| 8,374,678 B2* | 2/2013 | Graumann | .............. | A61B 6/12 378/205 |
| 8,548,629 B2* | 10/2013 | Ortmaier | ............... | A61B 6/102 324/662 |
| 8,559,596 B2* | 10/2013 | Thomson | .............. | G06T 7/0014 378/65 |
| 8,607,385 B2* | 12/2013 | Isham | ................. | A61G 13/123 5/621 |
| 8,737,705 B2* | 5/2014 | Pearson, Jr. | ........ | G06K 9/00221 382/128 |
| 8,747,382 B2* | 6/2014 | D'Souza | ............. | A61B 5/1135 604/500 |
| 8,788,020 B2* | 7/2014 | Mostafavi | .............. | A61B 5/113 324/309 |
| 8,824,630 B2* | 9/2014 | Maurer, Jr. | ......... | G06F 19/3481 378/20 |
| 8,917,813 B2* | 12/2014 | Maurer, Jr. | .............. | A61N 5/10 378/65 |
| 8,934,605 B2* | 1/2015 | Maurer, Jr. | .............. | A61N 5/10 378/65 |
| 9,028,144 B2* | 5/2015 | Choi | ...................... | A61B 6/032 378/205 |
| 9,433,395 B2* | 9/2016 | Kang | .................... | A61B 6/544 |
| 9,480,443 B2* | 11/2016 | Feuerlein | ............... | A61B 6/032 |
| 9,589,336 B2* | 3/2017 | Flohr | .................... | A61B 6/032 |
| 9,636,077 B2* | 5/2017 | Braun | .................... | A61B 6/032 |
| 9,642,584 B2* | 5/2017 | Niebler | ................ | A61B 6/4441 |
| 9,710,141 B2* | 7/2017 | Braun | .................... | A61B 6/032 |
| 9,763,599 B2* | 9/2017 | Graumann | .......... | A61B 5/0073 |
| 9,785,131 B2* | 10/2017 | Dirauf | .................... | A61B 5/704 |
| 9,811,902 B2* | 11/2017 | Flohr | ................... | G06K 9/4604 |
| 9,904,998 B2* | 2/2018 | Jockel | ...................... | A61B 6/08 |
| 9,907,518 B2* | 3/2018 | Gooßen | .............. | A61B 6/0492 |
| 9,924,914 B2* | 3/2018 | Dirkes | ................ | A61B 6/4452 |
| 9,943,271 B2* | 4/2018 | Dirauf | .................... | A61B 6/545 |
| 9,955,927 B2* | 5/2018 | Hendriks | ............... | A61B 6/025 |
| 10,004,465 B2* | 6/2018 | Krauss | .................... | A61B 6/032 |
| 10,034,712 B2* | 7/2018 | Gerken | ................ | A61B 6/54 |
| 10,062,168 B2* | 8/2018 | Brehm | .................. | A61B 6/503 |
| 10,098,607 B2* | 10/2018 | Grasruck | ............... | A61B 6/582 |
| 10,143,532 B2* | 12/2018 | Samsonov | ............ | A61B 90/39 |
| 10,181,074 B2* | 1/2019 | Braun | ................... | A61B 6/0457 |
| 10,194,882 B2* | 2/2019 | Kwak | .................... | A61B 6/54 |
| 10,213,169 B2* | 2/2019 | Braun | ................... | A61B 6/467 |
| 10,220,181 B2* | 3/2019 | Giap | .................... | A61N 5/1068 |
| 10,278,654 B2* | 5/2019 | Sadakane | ............. | A61B 6/4417 |
| 10,292,673 B2* | 5/2019 | Niizeki | ................ | A61B 6/4405 |
| 10,321,880 B2* | 6/2019 | Lerch | ................... | A61B 6/0407 |
| 10,366,489 B2* | 7/2019 | Boettger | ................. | G06T 7/50 |
| 10,376,217 B2* | 8/2019 | Schmidt | ............... | A61B 5/0555 |
| 10,424,118 B2* | 9/2019 | Hannemann | .......... | G06T 19/006 |
| 10,426,416 B2* | 10/2019 | Kong | ..................... | A61B 6/56 |
| 10,441,240 B2* | 10/2019 | Merckx | ................. | A61B 6/0457 |
| 10,512,417 B2* | 12/2019 | Hannemann | .......... | A61B 6/032 |
| 10,548,573 B2* | 2/2020 | Lerch | ................... | A61B 8/481 |
| 2005/0251914 A1 | 11/2005 | Schaller et al. | | |
| 2012/0264997 A1 | 10/2012 | Isham | | |
| 2016/0073979 A1 | 3/2016 | Braun et al. | | |

FOREIGN PATENT DOCUMENTS

DE 102014218557 A1 3/2016
WO WO 2016073841 A1 5/2016

* cited by examiner

POSITIONING OF AN EXAMINATION OBJECT FOR AN IMAGING METHOD

PRIORITY STATEMENT

The present application hereby claims priority under 35 U.S.C. § 119 to German patent application number DE 102016210131.5 filed Jun. 8, 2016, the entire contents of which are hereby incorporated herein by reference.

FIELD

At least one embodiment of the invention generally relates to a method for the positioning of an examination object for an imaging method. At least one embodiment of the invention furthermore generally relates to an object-positioning facility. Finally at least one embodiment of the invention generally relates to an imaging medical facility.

BACKGROUND

Modern imaging methods are frequently used to create two- or three-dimensional image data, which can be used to visualize an imaged examination object and also additionally for further applications.

Imaging methods are frequently based on the acquisition of X-rays, wherein so-called projection-scan data is created. For example, projection-scan data can be acquired via a computed-tomography system (CT system). With CT systems, typically a combination of an X-ray source and an oppositely arranged X-ray detector arranged on a gantry rotate about a scanning chamber in which the examination object (hereinafter referred to, without restricting the generality, as the patient) is located. In this case, the center of rotation (also called the "isocenter") coincides with a so-called system axis z. The patient is irradiated with X-rays from the X-ray source during one or more rotations, wherein projection-scan data or X-ray projection data is acquired via the oppositely located X-ray detector.

X-ray detectors used for CT imaging generally comprise a plurality of detection units, which are usually arranged in the form of a regular pixel array. The detection units in each case create a detection signal for the incident X-rays on the detection units with said signal being analyzed at specific time points with respect to the intensity and spectral distribution of the X-rays in order to obtain conclusions regarding the examination object and to create projection-scan data.

Other imaging techniques are, for example, based on magnetic resonance imaging. During the creation of magnetic resonance images, the body to be examined is exposed to a relatively high basic magnetic field, for example 1.5 tesla, 3 tesla, or in newer high magnetic field systems even 7 tesla. Then, a suitable antenna facility is used to emit a radio-frequency excitation signal which causes the nuclear spins of certain atoms excited into resonance by this radio-frequency field in said magnetic field to be tilted by a specific flip angle relative to the magnetic field lines of the basic magnetic field. The radio-frequency signal, the so-called magnetic resonance signal, radiated by the nuclear spins during relaxation is then received by suitable antenna facilities, which can also be identical to the transmitting antenna facility. The raw data acquired in this way is used to reconstruct the desired image data. For spatial encoding, during transmission and reception of the radio-frequency signals, the basic magnetic field is in each case superimposed by defined magnetic field gradients.

Patients have to be positioned in different ways for different types of imaging examination. For example, during CT imaging, to reduce the radiation dose, the patient's arms should be positioned above the head when the abdomen or thorax is to be scanned. On the other hand, it is advisable to position the arms pointing toward the feet when images are to be recorded of a patient's head. If images are to be depicted of a patient's extremities, other positions for the patient's body are specified. Therefore, it is important to know which relative position individual body parts of the patient should adopt for medical imaging. The specifications may vary in different hospitals, but should in particular be determined by the constitution of the respective patient if the patient is insufficiently mobile to adopt an ideal body position or is uncooperative and has to be secured. As a result, there is a large number of possibilities for positioning a patient so that medical staff are faced with a general positioning problem.

When positioning patients for medical imaging, it is inter alia also important for the axes of symmetry of the body to be correctly aligned relative to an imaging facility. As a rule, it is attempted to keep the axes of symmetry of the body as axes of symmetry in the medical image recordings as well so that they can also be identified on the images and used to identify any symmetry-breaching pathologies without laborious reworking of the images, i.e. restoration of the axes of symmetry by three-dimensional reformatting. Therefore, there is a problem with observing symmetry during the positioning of a patient for recording a medical image.

For example, when recording a CT image of a skull, the plane between the left and right halves of the skull is preferably arranged perpendicular to the CT slice plane, wherein ideally the nose points exactly upward or perpendicular to the surface of a recumbent patient. With such positioning, a hemisphere of the brain is in each case found in each axial slice of the CT image recording on the left and right half of the image as long as this does not contain any pathology that disrupts this. Symmetrical positioning of the patient on the patient table also facilitates the subsequent evaluation when imaging other regions of the body, such as, for example, an examination of the spine or the locomotor system.

While, conventionally, other steps during the course of a CT examination are very effectively defined by scan-protocol settings or reconstruction settings, to date, positioning has been, to a greater or lesser degree, a matter determined by the skills of the medical staff. Hence, this results in greater or lesser user-dependent deviations in positioning which can only be reduced by good training or lengthy experience on the part of users.

For correct positioning, at present operators must know how to position the patient. To ensure symmetrical positioning, a user can use a CT laser sight in or before a scanning plane.

SUMMARY

The inventor has discovered that, even when using this aid, a user must also be familiar with the correct positioning of the patient. In many less developed regions of the world, even though medical imaging facilities, such as, for example, CT systems are now available, as a result of poor organization and the absence of cognitive prerequisites, operators are often insufficiently trained and this can impair the quality of examinations of patients.

At least one embodiment of the present invention discloses a method for preparing an imaging method that enables the imaging to be performed to a large extent independently of the skills of the users.

At least one embodiment is directed to a method for positioning an examination object for an imaging method; at least one embodiment is directed to an object-positioning facility; and at least one embodiment is directed to an imaging medical facility.

With the method according to at least one embodiment of the invention for positioning an examination object for an imaging method, the external image of externally visible features of the examination object is recorded by means of an external-image recording unit. Hence, the recording of the external image is used for the preparation of the actual image recording of the examination object, for example a patient. While the actual imaging facility is intended to acquire the interior of the examination object, the recording of the external image is restricted to recording images of the externally visible features or the surface and contours of the examination object. In the simplest case, the recording of the external image can entail a two-dimensional image, hereinafter 2D image, which is depicted in monochrome or also in color. The method according to at least one embodiment of the invention is preferably applied to a medical imaging method.

The object-positioning facility according to at least one embodiment of the invention comprises an external-image recording unit for recording the external image of externally visible features of an examination object. In addition, part of the object-positioning facility according to the invention is a position-determining unit for determining a position and/or orientation of at least one part of the examination object assigned to the imaged features on the basis of the recording of the external image.

Furthermore, the object-positioning facility according to at least one embodiment of the invention includes a checking unit for checking whether the determined position and/or orientation of the at least one part of the examination object conforms to a reference position and/or reference orientation that is determined and defined in advance. The object-positioning facility according to the invention also comprises a position-correcting unit. The position-correcting unit is used to correct the position and/or orientation of the at least one part of the examination object if the determined position and/or orientation of the at least one part of the examination object does not conform to the predetermined reference position and/or reference orientation.

The imaging medical facility according to at least one embodiment of the invention, preferably a computed tomography system, comprises a scanning unit for acquiring a region to be examined of an examination object. It also comprises a control unit for controlling the scanning unit. Furthermore, the imaging medical facility according to at least one embodiment of the invention comprises an object-positioning facility according to at least one embodiment of the invention.

Components of the object-positioning facility according to at least one embodiment of the invention can be predominantly embodied in the form of software components. This in particular relates to the position-determining unit, the checking unit and the position-correcting unit. However, in principle, in particular when particularly fast calculations are required, the components can to some extent be implemented in the form of software-supported hardware, for example FPGAs or the like. Similarly, for example when only the acceptance of data from other software components is required, the required interfaces can be embodied as software interfaces. However, they can also be embodied as hardware-based interfaces actuated by suitable software.

An extensively software-based implementation has the advantage that it is also possible to retrofit control facilities used to date in a simple way via a software update in order to work in the manner according to at least one embodiment of the invention. Insofar, the object is also achieved by a corresponding computer program product with a computer program, which can be loaded directly into a storage facility of a control facility of an imaging system, preferably a computed tomography system, with program sections for carrying out all steps of the method according to at least one embodiment of the invention when the program is executed in the control facility. In addition to the computer program, a computer program product of this kind can optionally comprise additional parts such as, for example, documentation and/or additional components, including hardware components, such as, for example, hardware keys (dongles etc.) for using the software.

Transportation to the control facility and/or storage on or in the control facility can take place via a computer-readable medium, for example a memory stick, a hard disk or another kind of transportable or permanently installed data carrier on which the program sections of the computer program that can be read and executed by a computing unit of the control facility are stored. To this end, the computing unit can, for example, comprise one or more interacting microprocessors or the like.

The claims and following description each contain particularly advantageous embodiments and developments of the invention. Here, in particular the claims of one claim category can also be developed analogously to dependent claims of another claim category. In addition, it is also possible within the context of the invention for the different features of different example embodiments and claims also to be combined to form new example embodiments.

BRIEF DESCRIPTION OF THE DRAWINGS

The invention is described again in more detail below with reference to the attached figures and with reference to example embodiments. The figures show.

DETAILED DESCRIPTION OF THE EXAMPLE EMBODIMENTS

Figure 1:
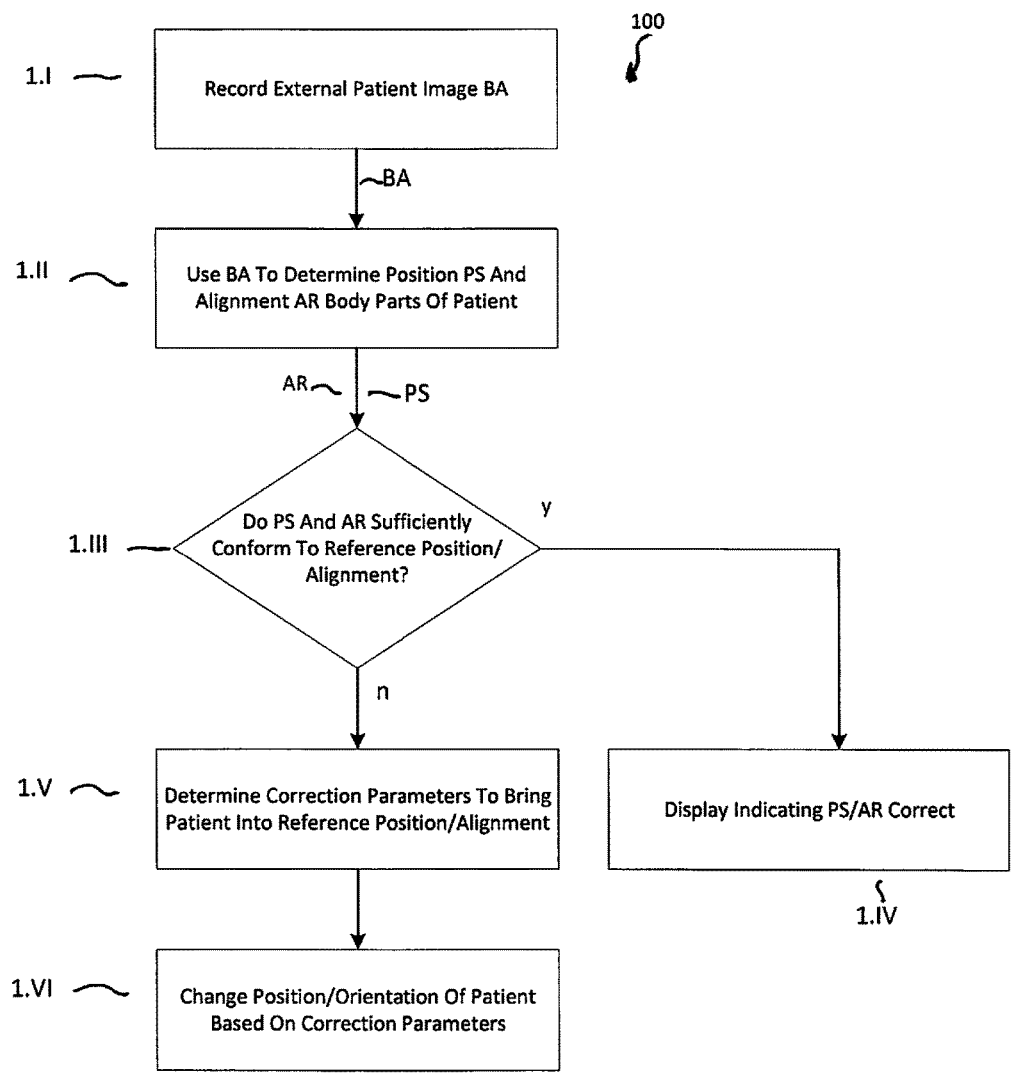
FIG. 1 a flow diagram illustrating a method for the positioning of an examination object for a medical imaging method in accordance with an example embodiment of the invention, FIG. 2 a block diagram illustrating an object-positioning facility in accordance with an example embodiment of the invention, FIG. 3 a computed tomography system in accordance with an example embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

With the method according to at least one embodiment of the invention for positioning an examination object for an imaging method, the external image of externally visible features of the examination object is recorded by means of an external-image recording unit. Hence, the recording of the external image is used for the preparation of the actual image recording of the examination object, for example a patient. While the actual imaging facility is intended to acquire the interior of the examination object, the recording of the external image is restricted to recording images of the externally visible features or the surface and contours of the examination object. In the simplest case, the recording of the external image can entail a two-dimensional image, hereinafter 2D image, which is depicted in monochrome or also in color. The method according to at least one embodiment of the invention is preferably applied to a medical imaging method.

Furthermore, a position and/or orientation of at least one part of the examination object assigned to the imaged features are determined on the basis of the recording of the external image. In this context, imaged features should in particular be features identifying the position, dimensions, orientation and boundaries or interfaces of the at least one part in the imaging facility in more detail. Furthermore, a position should also be understood to mean a relative position of individual parts of the examination object. In this context, a part of the examination object should be understood to mean a segment or a sub-unit of the examination object. In this context, at least one part should also be understood to mean the entirety of a plurality of parts of the examination object or even the entire examination object. The position and/or orientation of the at least one part should in particular be understood to mean the position and/or orientation of this part on a support on which the examination object is lying during imaging. In the case of medical imaging, the support can, for example, be a patient bed.

In a further step, a check is performed as to whether the determined position and/or orientation of the at least one part of the examination object conforms to a predetermined reference position and/or reference orientation.

The predetermined reference position and/or reference orientation of the respective part can, for example, be defined in advance from the viewpoint of minimum dose exposure or symmetry of the subsequent image recording by the imaging facility. The positioning and alignment of the reference position and/or the reference orientation are typically prespecified in a general set of regulations or a general protocol. For example, such a reference position and/or reference orientation can be defined relative to a marked position and direction. In the case of a CT device, this marked position can, for example, be a "twelve o'clock" position of a scanning unit in a gantry of the CT device. The marked direction can, for example, be the z-axis of the CT system.

If the check identifies that the determined position and/or orientation of the at least one part of the examination object does not conform to the predetermined reference position and/or reference orientation, the position and/or orientation of the at least one part of the examination object is corrected.

This enables a desired optimum position and/or orientation of parts of the examination object or even the entire examination object to be achieved. This is advantageously performed without an X-ray having to be taken in advance, thus also minimizing the dose exposure with respect to the recording of the external image necessary for the positional correction. A comparison of the acquired position and/or alignment of the at least one part with a reference position and/or reference orientation enables errors during the positioning of the examination object or parts thereof to be reduced or corrected, thus resulting in greater efficiency of the subsequent imaging recording by the imaging facility and hence in turn improving the efficiency of a subsequent analysis or evaluation. This simultaneously reduces the amount of training required for operators of the imaging facility since they are able to rely on the result of the comparison during the checking step or, in the case of the expressly preferred fully automatic performance of the method according to at least one embodiment of the invention, they do not require any experience or knowledge for correct positioning of the examination object, for example a patient. In addition, the method according to at least one embodiment of the invention also permits greater reproducibility and standardization of the imaging results within an institution or even when image data is exchanged between different institutions since the positioning and alignment are not defined in accordance with individual operator preferences but are standardized.

The object-positioning facility according to at least one embodiment of the invention comprises an external-image recording unit for recording the external image of externally visible features of an examination object. In addition, part of the object-positioning facility according to the invention is a position-determining unit for determining a position and/or orientation of at least one part of the examination object assigned to the imaged features on the basis of the recording of the external image.

Furthermore, the object-positioning facility according to at least one embodiment of the invention includes a checking unit for checking whether the determined position and/or orientation of the at least one part of the examination object conforms to a reference position and/or reference orientation that is determined and defined in advance. The object-positioning facility according to the invention also comprises a position-correcting unit. The position-correcting unit is used to correct the position and/or orientation of the at least one part of the examination object if the determined position and/or orientation of the at least one part of the examination object does not conform to the predetermined reference position and/or reference orientation.

The imaging medical facility according to at least one embodiment of the invention, preferably a computed tomography system, comprises a scanning unit for acquiring a region to be examined of an examination object. It also comprises a control unit for controlling the scanning unit. Furthermore, the imaging medical facility according to at least one embodiment of the invention comprises an object-positioning facility according to at least one embodiment of the invention.

The implementation of at least one embodiment of the invention in a CT system has the advantages that the scan duration of a CT system is relatively short. This is only a few seconds compared to recording with MRI systems, which can take several minutes. This is particularly advantageous with the examination of emergency patients with whom any time delay can be potentially fatal. In addition, CT systems are more widely used and less expensive than MRI systems. Since CT systems work with X-rays, it is particularly important with the application of this imaging technique to minimize the dose to which the patient is exposed. On the one hand, the object-positioning facility according to at least one embodiment of the invention contributes to this in that the advance recording of the external image does not require the emission of X-rays and, on the other hand, positioning with respect to dose exposure can be optimized without operators of the CT system requiring special training therefor.

By contrast, MR systems have the advantage that examinations with them do not entail exposure to X-rays and the soft-tissue contrast of an image recorded with an MR system is better than with a CT system. In the case of imaging with MR systems, symmetrical imaging can improve the quality of the image recording, since in this case, symmetrically arranged body parts can also be arranged symmetrically relative to the coil geometry of the transmitting and receiving coils or the gradient coils. During MR imaging, it is also possible to minimize the patient's RF exposure, wherein so-called SAR values are reduced.

Components of the object-positioning facility according to at least one embodiment of the invention can be predominantly embodied in the form of software components. This in particular relates to the position-determining unit, the checking unit and the position-correcting unit. However, in principle, in particular when particularly fast calculations are required, the components can to some extent be implemented in the form of software-supported hardware, for example FPGAs or the like. Similarly, for example when only the acceptance of data from other software components is required, the required interfaces can be embodied as software interfaces. However, they can also be embodied as hardware-based interfaces actuated by suitable software.

An extensively software-based implementation has the advantage that it is also possible to retrofit control facilities used to date in a simple way via a software update in order to work in the manner according to at least one embodiment of the invention. Insofar, the object is also achieved by a corresponding computer program product with a computer program, which can be loaded directly into a storage facility of a control facility of an imaging system, preferably a computed tomography system, with program sections for carrying out all steps of the method according to at least one embodiment of the invention when the program is executed in the control facility. In addition to the computer program, a computer program product of this kind can optionally comprise additional parts such as, for example, documentation and/or additional components, including hardware components, such as, for example, hardware keys (dongles etc.) for using the software.

Transportation to the control facility and/or storage on or in the control facility can take place via a computer-readable medium, for example a memory stick, a hard disk or another kind of transportable or permanently installed data carrier on which the program sections of the computer program that can be read and executed by a computing unit of the control facility are stored. To this end, the computing unit can, for example, comprise one or more interacting microprocessors or the like.

The claims and following description each contain particularly advantageous embodiments and developments of the invention. Here, in particular the claims of one claim category can also be developed analogously to dependent claims of another claim category. In addition, it is also possible within the context of the invention for the different features of different example embodiments and claims also to be combined to form new example embodiments.

In one preferred embodiment of the method according to the invention for the positioning of an examination object for an imaging method, the predetermined reference position and/or orientation includes a predetermined alignment of the at least one part of the examination object with respect to an axis of symmetry of the at least one part. I.e., the axis of symmetry of the at least one part is aligned in accordance with an axis of symmetry of the imaging such that, in the subsequent image recording of the imaging facility, the axis of symmetry of the at least one part is arranged centrally. To this end, the axis of symmetry of the at least one part is arranged in accordance with a position and orientation of the image recording region determined by the geometry of the arrangement of the imaging facility, in particular the scanning unit of the imaging facility.

Within the context of the method according to at least one embodiment of the invention, this is achieved in that the alignment of the examination object, for example a patient, in the imaging facility is made or changed such that the position and alignment of the examination object or at least of the at least one part corresponds to this reference position and/or orientation. The predetermined reference position can also include a predetermined relative position of individual parts of the examination object with respect to one another. For example, in particular with the imaging of a patient, it is frequently important for individual body parts to be positioned with respect to one another such that only the body parts to be imaged are exposed to X-rays in order to reduce the dose exposure of the patient. In this case, body parts that are not to be imaged are arranged such that they do not lie within the region to be imaged.

To create the external image recording, the external-image recording unit used preferably has sensors for recording images of a 3D surface and/or for creating a 2D image recording. A recording of a 3D surface of the examination object permits a more accurate determination of the orientation of the examination object thus enabling a precise correction of the orientation of the examination object in the context of the method according to at least one embodiment of the invention. The sensors can for example include optical sensors. Advantageously, when optical sensors are chosen for the recording of the external image, no high-energy rays or waves that stress the examination object are required, thus reducing the dose to which the examination object is exposed.

In one embodiment of the method according to the invention for the positioning of an examination object for an imaging method, the examination object includes a patient and at least one part of the examination object includes at least one body part of the patient. In particular, with medical imaging of a patient, it is particularly important for the patient or individual body parts of the patient to be correctly positioned. On the one hand, with the use of X-rays, this enables the dose to which the patient is exposed to be reduced to a minimum or, on the emission of radio-frequency magnetic fields, enables the SAR values to be reduced, and on the other hand, it is advisable also to arrange axes of symmetry of the human body in the image display such that the image is produced symmetrically in accordance with the patient's body symmetry. Deviations from this symmetry can then, for example, be interpreted as pathology or at least be examined in more detail as irregularities.

In one variant of the method according to an embodiment of the invention for the positioning of an examination object for an imaging method, during the determination step, anatomical landmarks are extracted from the recording of the external image and said anatomical landmarks are used to compile a virtual 3D body model from which the position and/or orientation of the at least one body part is determined.

These landmarks of the examination object can, for example, be determined automatically using the recording of the external image and the position and/or orientation of the at least one body part of the patient and/or the relative position of individual body parts of the patient can be determined on the basis of at least one distance between the landmarks. Landmarks can be understood to be individual body features of the patient that are easy to identify or localize in an image display such as, for example, the eyes, nose, knees or feet. The landmarks can, for example, mark positions of specific sub-regions of the patient and hence provide additional details during the determination of relevant dimensions, which then in turn permit a more exact determination of the positions and dimensions of the body parts of the patient. Specifically, it is possible for the feet or head, for example, of a patient to be automatically identified in the image recording. The length between the landmarks then indicates the longitudinal extension of the patient. This data can then in turn be used to determine or assess positions and/or orientations of additional body parts, such as, for example, of the stomach or chest or legs.

The landmarks can be automatically detected using heuristics including at least one of the following methods:
the detection of landmarks with the aid of edge detectors,
threshold filtering,
an automatic learning method.

The methods named can be used to find suitable features for the detection of the landmarks automatically. With the use of edge detectors, texture differences, in particular contrast differences indicative of the presence of boundary lines between different objects or structures are determined in the recorded image and which can be used in the segmentation of an image recording.

Threshold filters are also used for the segmentation of images. In this case, the association of a pixel to a segment is determined by comparing a gray value or another feature with a threshold value. The simplicity of threshold-value methods enables them to be implemented quickly and the results of segmentation can be calculated with little effort.

When an automatic learning method is used, suitable features for the detection of the landmarks are determined automatically using annotated training images.

The methods named are used for pattern identification using the external image data acquired with the aid of the recording of the external image. Landmarks typically comprise characteristic structures that can be identified by means of the methods listed.

In one preferred variant of the method according to an embodiment of the invention for the positioning of an examination object for an imaging method, during the checking step it is determined whether the at least one body part should be arranged differently or whether a relative position of individual body parts of the patient with respect to one another should be changed. This checking step can, for example, be performed by a comparison of the determined position of the body part of the patient with a reference position. If the comparison determines a deviation exceeding a predetermined threshold, preferably a correction or a displacement of the body part or the entire patient is determined automatically with which the deviation determined can be corrected.

Additionally, it is preferably also determined whether one or more axes of symmetry of the at least one body part of the patient are aligned correctly with respect to the medical imaging facility used for the imaging. With this check, there is first a comparison of the determined orientation of the body part of the patient with a reference position which permits symmetry of the image of the respective body part with respect to one or more axes of symmetry of the medical imaging facility. If the comparison determines a deviation exceeding a predetermined threshold, a correct or rotation and/or displacement of the body part or the entire patient with which the determined deviation can be corrected is preferably determined automatically.

This achieves an optimum or standardized positioning and alignment of the patient without operators requiring corresponding knowledge.

In one effective variant of the method according to an embodiment of the invention for the positioning of an examination object for an imaging method, the positioning and/or alignment of the patient during the positioning of the at least one body part is displayed in real time. Furthermore, the reference position and/or reference alignment of the body part is displayed simultaneously so that it may be identified from the two image depictions whether it is necessary to change the position and/or alignment of the at least one body part and/or change a relative position of individual body parts of the patient. This enables operators to identify from the depicted deviation from a nominal position or nominal alignment how they need to change the position and alignment of the patient or individual body parts of the patient in order to achieve a desired standard positioning.

The real-time display enables operators to use this as a type of navigation aid and quickly find the correct positioning of the patient without any subsequent laborious corrections. The position and alignment of the patient are preferably displayed such that users are able to see this display from a patient bed arranged in the respective medical imaging facility so that users can implement the information displayed to them directly, for example, by repositioning the patient or individual body parts of the patient without having to move away from the patient bed. This accelerates the sequence of work for the positioning of the patient and improves user friendliness.

If it is necessary to change the position and/or alignment of the at least one body part and/or the relative position of individual body parts, preferably suggested corrections are then displayed. Operators can use the suggested corrections to reposition the patient appropriately so that the patient's position corresponds to the predefined reference position or reference orientation. With this variant, operators advantageously do not have to know the correct position of the patient or translate it into the specific existing geometry of the medical imaging facility but are able to rely on the suggestions displayed to them.

In one embodiment of the method according to an embodiment of the invention for the positioning of an examination object for an imaging method, the recording of the external image and/or the step for determining the position and/or orientation of the at least one part and/or the checking step and/or the corrective step is performed semi-automatically or fully automatically. This relieves operators to a greater or lesser degree of the need to perform corrective steps or corrective measures and it is also possible to use inexperienced operators since the positioning of an examination object, for example a patient, or the correction of the position thereof takes place substantially automatically and hence independently of operators' specialized knowledge and experience. If, for example, there are ethical objections to a fully automatic patient arrangement, it is also possible for all steps apart from the corrective step to be automated and in this case the positional correction of the patient can be performed manually.

With the method according to an embodiment of the invention the external-image recording unit can use at least one of the following facilities:
a camera,
a depth camera,
a non-contact electromagnetic sensor,
an ultrasound distance-measuring unit,
a radar-sensor facility,
a depth camera and additionally a 2D camera.

The majority of the appliances named have the advantage that their operation does not entail any additional stress for the patient.

The camera used can, for example, be a digital camera with which a two-dimensional image is recorded in which specific anatomical features, the aforementioned landmarks, can be identified. The camera can, for example, also be part of a smartphone or a tablet computer.

When recording via a depth camera, a camera is used that supplies a three-dimensional image, hereinafter also 3D image. A depth camera creates an image in which each image point indicates the distance of the closest object to the camera. This information enables the depth image to be transferred to a point cloud in world coordinates. Similarly to the case in the 2D image, it is possible for landmarks and distances to be determined in this 3D image.

In one particularly practicable embodiment of the method according to the invention, for the correct positioning and/or alignment of the at least one body part of the patient and/or for the correct relative positioning of individual body parts of the patient, one or more inflatable patient support cushions with a plurality of air chambers are placed under the patient and, during the corrective step, it is determined, preferably automatically, in dependence on a position to be corrected and/or alignment of the at least one body part which cushions and which air chambers have to be inflated with which defined air quantity in order to achieve correct positioning and/or alignment of the patient or a correct relative position of individual body parts of the patient. Advantageously, such cushions can be placed under different body parts of a patient.

Selective, preferably automated inflation of individual chambers performed on the basis of the positional correction determined according to an embodiment of the invention enables the respective patient support cushion to be used to bring the respective body part into the correct position or to align it correctly without requiring manual intervention on the part of the operators themselves. This renders the corrective step automatic and independent of operators' qualifications so that observance of fixed standards is ensured during the positioning of a patient.

In one particularly preferred variant of the method according to an embodiment of the invention, the contours of the examination object are determined on the basis of the recording of the external image and the contours determined are used to determine the dimensions of the examination object. The contours and dimensions of the examination object can, for example, be used to obtain more precise information with respect to the position and orientation of individual parts of the examination object.

It is also advantageous for the distance of the image-recording unit from the examination object to be taken into account during the determination of the position and/or orientation of parts of the examination object. I.e., the image scale of the recording of the external image is determined with knowledge of the distance of the examination object from the external-image recording unit. Further parameters to be taken into account can, for example, be the focal distance of the lens of the external-image recording unit. The named parameters and the position and/or orientation determined on the recording of the external image can then be used to draw conclusions regarding the actual position and/or orientation of the examination object or parts of the examination object. If the external-image recording unit is located at a different position than the scanning unit of the imaging facility, the recording of the external image first has to be translated into the perspective and position of the scanning unit. In this case, the determination of the distance or determination of the true position of the respective parts of the examination object is useful.

In one particularly advantageous variant of the method according to an embodiment of the invention, the external-image recording unit is used to record external images of the examination object from different directions. The different directions can, for example, include a frontal view and a profile view. Recording the external images from a plurality of directions then enables the spatial reconstruction of an exact position and orientation of the examination object or individual parts of the examination object.

It is also possible to use methods such as, for example, "Shape from Shading" to determine a 3D profile of the examination object from an individual recording of the external image. In this case, the lighting ratios can be used to draw conclusions regarding the extension of an examination object also in the direction of the optical axis of the external-image recording unit using one single recording of the external image. This method includes a reconstruction of a three-dimensional surface using the shadow cast in a recording of the external image.

The conventional methods used in the recording of a 3D image are the structured light method or the time of flight method. With the structured light method, line patterns are created on the object to be recorded. These lines intersect, for example, on the object. Following the three-dimensional extension of the object, the intersecting lines become blurred and a three-dimensional image of the object can be derived from this. With the time of flight method, a run-time measurement of light rays emitted in the direction of an object to be recorded is performed. A determined phase difference of emitted and received light waves enables conclusions to be drawn with respect to the distances present between the detection system used for the measurement and the object to be imaged.

It is also possible for the non-contact electromagnetic sensors, ultrasound distance-measuring units or radar sensor facilities named to be used to obtain a 3D image display of the patient.

A depth camera can additionally also include a further 2D camera. If the two cameras are calibrated with respect to one another, the determination of landmarks or contours can take account of the 2D image and 3D image simultaneously thus improving the accuracy of the determination of dimensions and positions since 2D cameras generally achieve a higher resolution than 3D cameras.

In one special embodiment of the method according to an embodiment of the invention, a virtual model of the examination object adapted to the data in the recording of the external image is used for a particularly precise determination of the positioning and/or orientation of the at least one part of the examination object. If the examination object is a human, a virtual model of this kind is generally known as an avatar.

An avatar can be imagined to be a type of virtual articulated doll which is imposed in the external image data recorded, in particular 3D image data, in accordance with the patient's position. An avatar can include a statistical shape model containing realist proportions for the individual limbs and their interrelationships from a database of recordings of natural people. Positioning an avatar of this kind in the external image data recorded can be used to compensate for inaccuracies in the recordings of external images, for example caused by noise or overexposure. An avatar provides additional information on the extension, position and orientation of individual regions of a patient's body. The structured, hierarchical structure of the avatar enables the position, relative position and orientation of individual body regions and limbs to be determined more easily and more precisely.

It is particularly advantageous for the virtual model to include personalized information with respect to the patient determined on the basis of a database which influence the choice of position and/or orientation of the patient during medical imaging. To this end, relevant medical information such as image data, the course of a disease, etc, can be stored in an extensive database. Then, the person in the database who appears most similar to a patient to be examined in the sense of a similar body structure is determined.

Alternatively or additionally, it is also possible to use an automatic learning method, a so-called deep learning method or a reinforcement learning method for the comparison with the database. In this case it is, for example, possible on the one hand to take account of a body shape of the patient derived from the external image data recorded and, on the other hand, to use a body shape derived from the medical image data stored in the database. It is additionally also possible, for example, to take account of a clinical picture of the patient and, for example, to search for a patient with a similar body shape and comparable clinical picture in the database. When one or more similar patients have been found in the database, the relevant parameters thereof, for example the dimensions, position and shape of individual body regions or body parts are transferred to the personalized avatar.

FIG. 1 shows a flow diagram 100 illustrating an example embodiment of a method for the positioning of a patient for a CT imaging method. The described sequence of the method takes place before medical imaging so that the patient is arranged in an optimum position for the CT imaging.

With the example embodiment illustrated in FIG. 1, a patient is to be positioned for a subsequent recording of the head. To this end, the arms of the patient should be positioned next to the body to ensure that they are not unnecessarily exposed to X-rays during the CT imaging. Furthermore, viewed from above, the head region of the patient should be arranged axially symmetrically to the z-axis of the CT system so that the axis of symmetry of the head coincides with the center axis of the CT image.

In Step 1.I, first the external image BA of the patient is recorded by means of a camera. The camera is arranged relative to the patient such that the camera can be used to record body parts of the patient to be positioned, in this case the head and arms on the acquired recording of the external image BA. In Step 1.II, the recording of the external image BA is used to determine a position PS and an alignment AR of individual body parts, in this case the arms and head of the patient. For example, the patient initially had the arms folded behind the head; this was recorded in the recording of the external image BA and automatically determined in Step 1.II. This is performed using a 3D model of a patient, which is registered on the recording of the external image BA. It is determined from the position of the arms of the 3D model that the patient's arms are folded behind the head.

In Step 1.III, a comparison of the 3D model of the patient with a reference position and reference alignment is used to check whether the determined position PS and alignment AR of the patient conforms sufficiently to the reference position and reference alignment. If this is the case, as identified in FIG. 1 with "y", the method moves on to Step 1.IV in which it is displayed to the operator that the position PS and alignment AR of the patient are correct. If the position PS or the alignment AR of the patient do not conform to reference position or the reference alignment, as indicated in FIG. 1 with "n", the method moves on to Step 1.V in which correction parameters of a correction process are determined in order to bring the patient into the reference position or reference alignment. For example, a translation direction, a translation length and an angle of rotation by which the patient or the arms or head thereof is to be changed is determined so that the reference position or reference alignment is achieved.

Finally, in a Step 1.VI, the position and orientation of the head and arms of the patient O are changed in accordance with the correction parameters determined in Step 1.V so that the desired position and alignment of both the head and the patient's arms are achieved.

Figure 2:
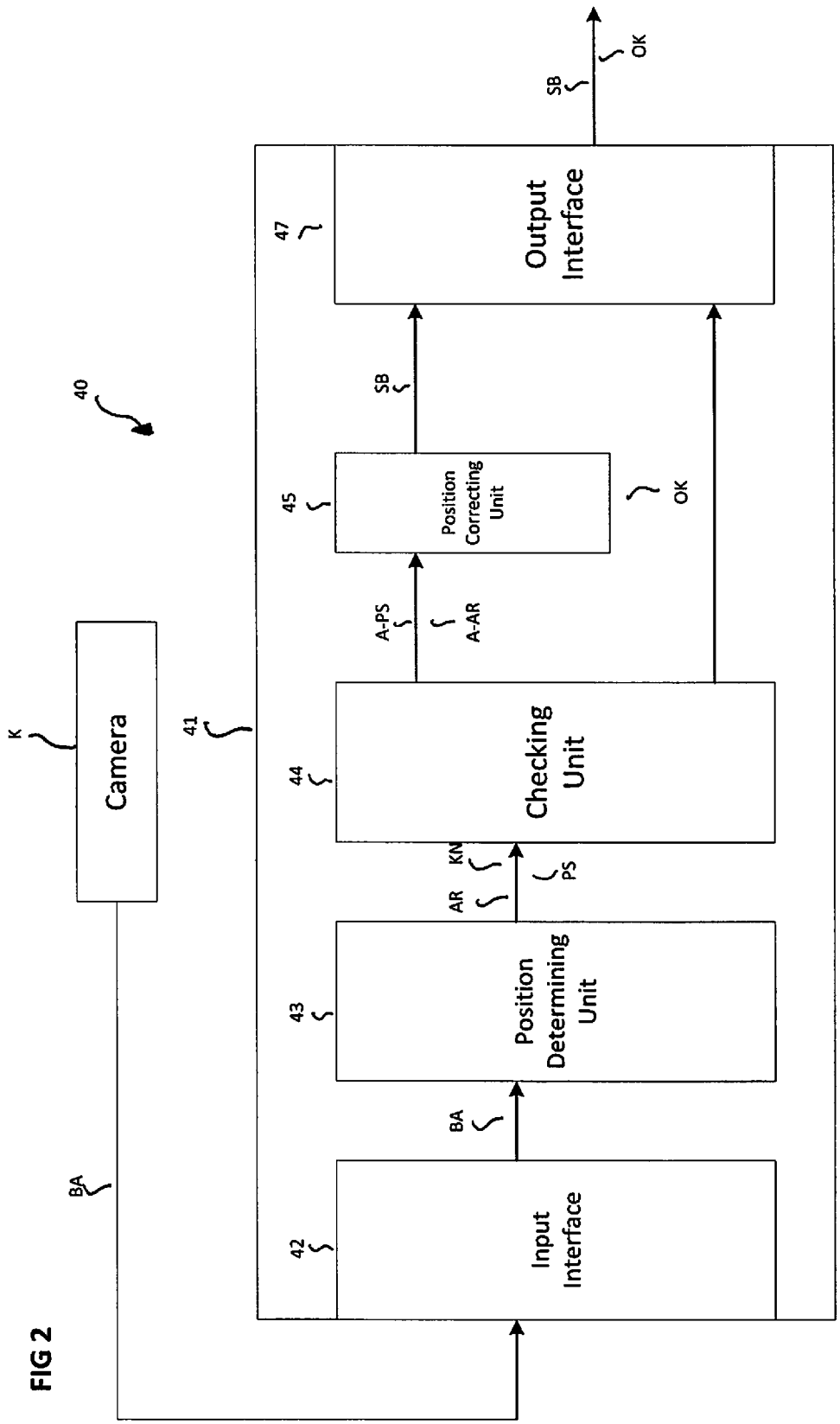

FIG. 2 shows an object-positioning facility 40 in accordance with an example embodiment of the invention. The object-positioning facility 40 can, for example, be part of a control facility 20 of a CT imaging facility 1 (see FIG. 3). The object-positioning facility 40 includes an object-positioning control unit 41 and additionally also a camera K for recording an external image BA of a patient from whom a CT image is subsequently to be created. The external image BA recorded by the camera K is sent to the object-positioning control unit 41. The object-positioning-determining unit 41 includes an input interface 42 to receive data from the external image BA. The data from the external-image BA is then sent internally to a position-determining unit 43. The position-determining unit 43 determines on the basis of the data from the external-image BA, a position PS and an alignment AR of body parts of the patient whose position and alignment is to conform to a predetermined reference position or reference alignment KN during the subsequent CT imaging.

The position data PS and alignment data AR are then sent to a checking unit 44. The checking unit 44 checks whether the determined position PS and orientation AR conform to a reference position and a reference orientation. If the checking unit 44 determines that the position of the patient and the alignment thereof also corresponds sufficiently to the reference values, a message OK (see FIGS. 2 and 3) is sent via an output interface 47 indicating that the position and alignment of the patient is in order. This message is, for example, displayed on the screen of a control facility 20 (see FIG. 3) of the CT imaging facility 1. If further correction is required, information relating to a deviation A-PS, A-AR of the position and alignment of the patient from reference values is sent to a position-correcting unit 45. On the basis of the deviations A-PS, A-AR of the position and alignment of the patient determined by the checking unit 44, the position-correcting unit 45 creates control commands SB, which are sent via the output interface 47 to an actuator unit, for example an inflatable cushion KS under the patient (see FIG. 3) in order to correct the position and alignment of the patient accordingly.

Figure 3:
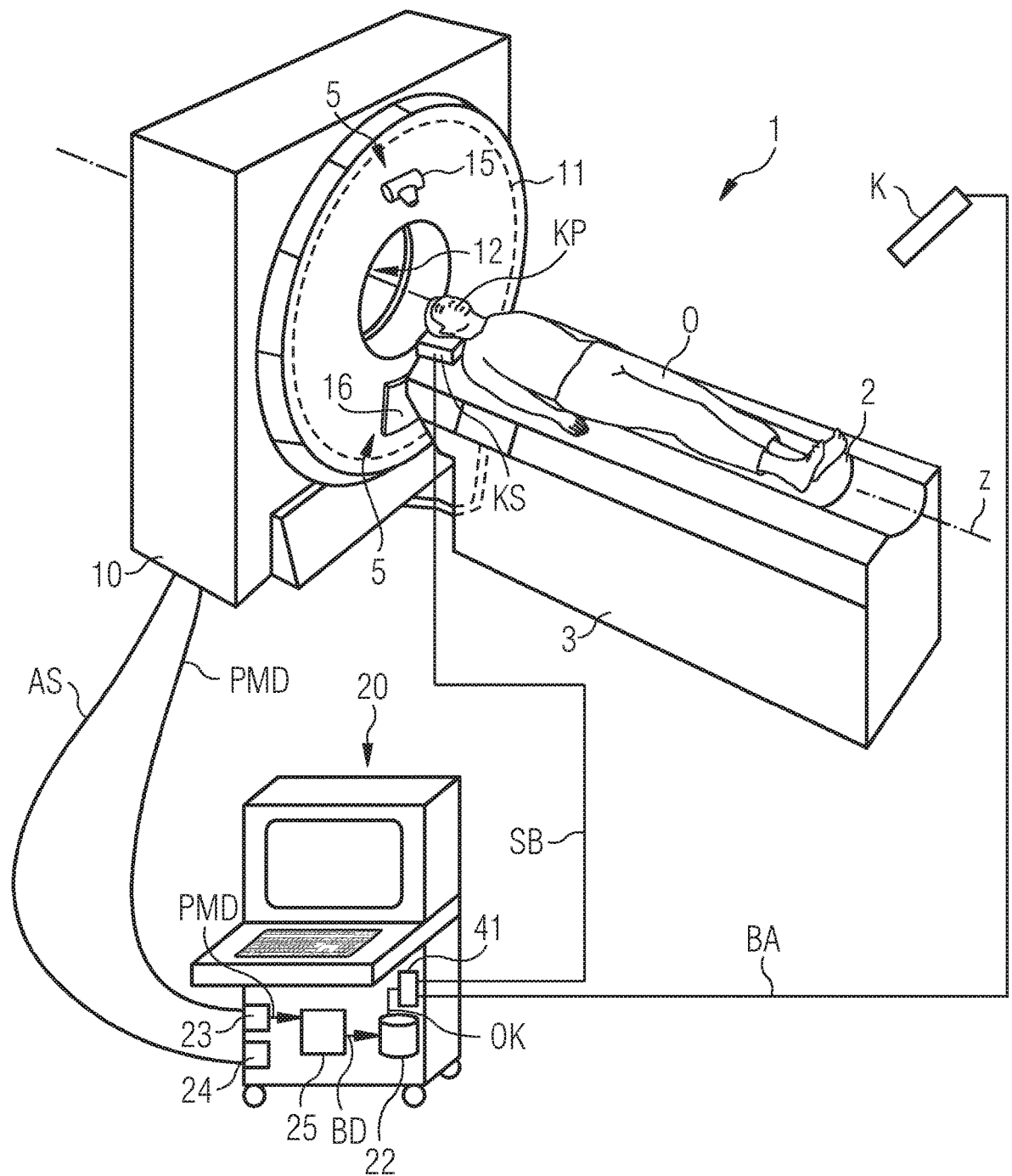

FIG. 3 shows a computed tomography system 1 in accordance with an example embodiment of the invention, which also includes an object-positioning-determining unit 41 corresponding to the unit 41 shown in FIG. 2 in accordance with an example embodiment. In this case, the computed tomography (CT) system 1 substantially consists of a conventional scanning unit 10, in which, on a gantry 11, a projection-data-acquisition unit 5 with a detector 16 and an X-ray source 15 lying opposite the detector 16 rotate about a scanning chamber 12. Located in front of the scanning unit 10, there is a patient support facility 3 or a patient bed 3, the upper part of which 2 can be pushed with a patient O located thereupon toward the scanning unit 10 in order to move the patient O through the scanning chamber 12 relative to the detector 16. The scanning unit 10 and the patient table 3 are controlled by a control facility 20 which issues acquisition-control signals AS via a conventional control interface 24 in order to control the CT system 1 in accordance with pre-specified scan protocols.

In the case of spiral acquisition, moving the patient O along the z-direction corresponding to the system axis z longitudinally through the scanning chamber 12 and the simultaneous rotation of the X-ray source 15 produces a helical path for the X-ray source 15 relative to the patient O during the scan. In parallel, in this case, the detector 16 always rotates oppositely to the X-ray source 15 in order to acquire projection-scan data PMD which is then used to reconstruct volume and/or slice-image data. It is also possible for a sequential scanning method to be performed in which a fixed position is approached in the z-direction and then, during a rotation, a part-rotation or several rotations at the respective z-position, the necessary projection-scan data PMD is acquired in order to reconstruct a sectional view at this z-position or reconstruct image data BD from the projection-scan data PMD for several z-positions. The method according to an embodiment of the invention can in principle also be used with other CT systems, for example, with a plurality of X-ray sources and/or detectors and/or with a detector forming a complete ring.

The projection-scan data PMD acquired by the detector 16 during imaging (hereinafter also raw data) is sent to the control facility 20 via a raw-data interface 23. This raw data PMD is then, optionally after suitable preprocessing (for example, filtering and/or beam-hardening correction), further processed in an image-reconstruction unit, which, in this example embodiment, is implemented in the control facility 20 in the form of software on a processor. The image-reconstruction unit 25 reconstructs image data BD on the basis of the raw data PMD by means of a reconstruction method. The reconstruction method used can, for example, be a reconstruction method based on filtered back projection.

The image data BD acquired is stored in a memory 22 of the control facility 20 and/or output in the usual way on the screen of the control facility 20. It can also be fed into a network, for example a radiology information system (RIS), connected to the computed tomography system 1 via an interface not shown in FIG. 3 and stored in a mass storage system that can be accessed there or output as images on printers connected or filming stations connected thereto. This enables the image data BD to be further processed in any way desired and then stored or output.

Additionally, FIG. 3 also shows an object-positioning-determining unit 41 which receives external image data BA from the patient O from a camera K. As described in connection with FIGS. 1 and 2, the object-positioning-determining unit 41 uses the external image data BA as the basis for the creation of control commands SB with which an inflatable cushion KS, in this case under the head KP of the patient O, is controlled. In FIG. 3, the object-positioning-determining unit 41 is illustrated as part of the control facility 20. The reference values used by the object-positioning-determining unit 41, such as, for example, the reference position and alignment of individual body parts of a patient, can, for example, be stored in the memory 22 and retrieved from the memory 22, along with the OK message of FIG. 2, by the object-positioning-determining unit 41 for a determination of a positional correction or control commands SB corresponding thereto.

Finally, reference is made once again to the fact that the above-described method for the positioning of an examination object for an imaging method and the described object-positioning facility 40 and described computed tomography system 1 are only example embodiments of the invention and that the invention can be varied by the person skilled in the art without departing from the scope of the invention as specified by the claims. For example, the imaging system used can also be a magnetic resonance imaging system, a PET-CT system, a SPECT-CT system or a 2D X-ray imaging system.

For the purpose of completeness, reference is also made to the fact that the use of the indefinite article "a" or. "an" does not exclude the presence of a plurality of the relevant features. Likewise, the term "unit" does not exclude the possibility that this may consist of a plurality of components which may be spatially distributed if applicable.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for positioning of an examination object for an imaging method, comprising:
   recording an external image of externally visible features of the examination object via an external-image recording unit;
   determining at least one of a position and an orientation of at least one part of the examination object assigned to the externally visible features of the examination object based upon the external image recorded;
   checking whether or not the at least one of the position and the orientation determined, of the at least one part of the examination object, conforms to a respective at least one of a reference position and a reference orientation; and
   correcting the at least one of the position and the orientation determined, of the at least one part of the examination object, in response to the checking indicating that the at least one of the position and the orientation determined, of the at least one part of the examination object, does not conform to the respective at least one of the reference position and the reference orientation.

2. The method of claim 1, wherein the respective at least one of the reference position and the reference orientation includes at least one of an alignment of the at least one part of the examination object with respect to an axis of symmetry of the at least one part of the examination object and a relative position of individual parts of the examination object with respect to another axis of symmetry.

3. The method of claim 2, wherein the examination object includes a patient, and wherein the at least one part of the examination object includes at least one body part of the patient.

4. The method of claim 3, wherein the determining, includes extracting anatomical landmarks from the external image recorded and using the anatomical landmarks to compile a virtual 3D body model from which at least one of the position and the orientation of the at least one part of the examination object is determined.

5. The method of claim 4, wherein the checking includes determining at least one of:
   whether the at least one body part of the patient should be arranged differently, and
   whether the axis of symmetry of the at least one body part of the patient is aligned correctly relative to a medical imaging facility, and
   whether individual body parts of the patient are arranged correctly relative to one another.

6. The method of claim 3, wherein the checking includes determining at least one of:
   whether the at least one body part of the patient should be arranged differently, and
   whether the axis of symmetry of the at least one body part of the patient is aligned correctly with respect to a medical imaging facility, and
   whether individual body parts of the patient are arranged correctly relative to one another.

7. The method of claim 3, further comprising:
   displaying at least one of the position and the orientation of the patient determined, during positioning of the at least one body part of the patient, in real time, wherein at least one of the reference position and the reference orientation of the at least one body part of the patient is displayed simultaneously to permit identifying, from two image depictions, a need to change at least one of the position and the orientation of the at least one body part of the patient determined.

8. The method of claim 7, further comprising:
   displaying suggested correction, in response to identifying a need to change at least one of the position and the orientation of the at least one body part of the patient.

9. A method of claim 3, wherein the correcting of the at least one of the position and the orientation determined includes placing at least one inflatable patient support cushion with a plurality of air chambers under the patient and determining, during the correcting and in dependence of the at least one of the position and the orientation of the at least one body part determined, which air chambers of the plurality of air chambers have to be inflated with which defined air quantity in order to achieve correct at least one of the positioning and the orientation of the patient determined.

10. The method of claim 2, wherein the external-image recording unit includes sensors for recording the external image of the externally visible features of the examination object from at least one of a 3D surface and a 2D image.

11. The method of claim 2, further comprising:
performing at least one of the recording of the external image of the externally visible features of the examination object, the determining of at least one of the position and the orientation of the at least one part of the examination object, the checking, and the correcting semi-automatically or fully automatically.

12. The method of claim 1, wherein the external-image recording unit includes sensors for recording the external image of the externally visible features of the examination object from at least one of a 3D surface and a 2D image.

13. The method of claim 1, further comprising:
performing at least one of the recording of the external image of the externally visible features of the examination object, the determining of at least one of the position and the orientation of the at least one part of the examination object, the checking, and the correcting semi-automatically or fully automatically.

14. The method of claim 1, wherein the external-image recording unit includes at least one of:
a camera,
a depth camera,
a non-contact electromagnetic sensor,
an ultrasound distance-measuring unit,
a radar-sensor facility, and
a depth camera and additionally a 2D camera.

15. The method of claim 1, wherein the examination object includes a patient, and the at least one part of the examination object includes at least one body part of the patient.

16. The method of claim 15, wherein the determining includes extracting anatomical landmarks from the external image recorded and using the anatomical landmarks to compile a virtual 3D body model from which at least one of the position and the orientation of the at least one part of the examination object is determined.

17. A non-transitory computer-readable medium storing program sections, readable and executable by a computing unit, for carrying out the method of claim 1 when the program sections are executed by the computing unit.

18. A non-transitory computer-readable medium storing program sections, readable and executable by a computing unit, for carrying out the method of claim 2 when the program sections are executed by the computing unit.

19. A non-transitory computer-readable medium storing program sections, readable and executable by a computing unit, for carrying out the method of claim 7 when the program sections are executed by the computing unit.

20. An object-positioning facility, comprising:
an external image recorder, including at least one of a camera, an electromagnetic sensor, and an ultrasound device, to record an external image of externally visible features of an examination object and to produce a recorded external image of externally visible features of the examination object; and
at least one processor:
to determine at least one of a position and an orientation of at least one part of the examination object assigned to the externally visible features of the examination object based upon the recorded external image of externally visible features of the examination object and to produce a determined at least one of a position and an orientation;
to determine whether or not the at least one of the position and the orientation determined conforms to a respective at least one of a reference position and a reference orientation; and
to correct the at least one of the position and the orientation determined, of the at least one part of the examination object, in response to determining that the at least one of the position and the orientation determined, of the at least one part of the examination object, does not conform to the respective at least one of the reference position and the reference orientation.

21. An imaging medical facility, comprising:
a scanner to acquire a region to be examined of an examination object;
a control facility to control the scanner; and
the object-positioning facility of claim 20.

22. A computed tomography system, comprising:
a computed tomography device to acquire a region to be examined of an examination object;
a control facility to control the computed tomography device; and
the object-positioning facility of claim 20.

23. An object-positioning facility, comprising:
an external-image recorder, including at least one of a camera, an electromagnetic sensor, and an ultrasound device, to record an external image of externally visible features of an examination object and to produce a recorded external image of the externally visible features of the examination object;
a memory storing computer-readable instructions; and
one or more processors configured to execute the computer-readable instructions such that the one or more processors are configured to:
determine at least one of a position and an orientation of at least one part of the examination object assigned to the externally visible features of the examination object based upon the external image recorded and to produce a determined at least one of a position and an orientation;
determine whether or not the at least one of the position and the orientation determined, conforms to a respective at least one of a reference position and a reference orientation; and
correct the at least one of the position and the orientation determined, of the at least one part of the examination object, in response to determining that the at least one of the position and the orientation determined, of the at least one part of the examination object, does not conform to the respective at least one of the reference position and the reference orientation.

24. An imaging medical facility, comprising:
a scanner to acquire a region to be examined of an examination object;
a control facility to control the scanner; and
the object-positioning facility of claim 23.

25. A computed tomography system, comprising:
a computed tomography device to acquire a region to be examined of an examination object;
a control facility to control the computed tomography device; and
the object-positioning facility of claim 23.

* * * * *